US009541615B2

(12) United States Patent
Idiyatullin et al.

(10) Patent No.: US 9,541,615 B2
(45) Date of Patent: Jan. 10, 2017

(54) SYSTEM AND METHOD FOR MULTI-ROI MRI IMAGING USING AN RF LOOP COIL

(71) Applicants: Djaudat Idiyatullin, New Brighton, MN (US); Curt Corum, Shoreview, MN (US); Michael Garwood, Medina, MN (US); Donald Nixdorf, St. Paul, MN (US); Gregor Adriany, Minneapolis, MN (US)

(72) Inventors: Djaudat Idiyatullin, New Brighton, MN (US); Curt Corum, Shoreview, MN (US); Michael Garwood, Medina, MN (US); Donald Nixdorf, St. Paul, MN (US); Gregor Adriany, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 371 days.

(21) Appl. No.: 14/163,447

(22) Filed: Jan. 24, 2014

(65) Prior Publication Data
US 2014/0213888 A1 Jul. 31, 2014

Related U.S. Application Data

(60) Provisional application No. 61/756,886, filed on Jan. 25, 2013.

(51) Int. Cl.
*G01R 33/34* (2006.01)
*G01R 33/48* (2006.01)
(Continued)

(52) U.S. Cl.
CPC ......... *G01R 33/34084* (2013.01); *A61B 5/055* (2013.01); *G01R 33/341* (2013.01); *G01R 33/3415* (2013.01)

(58) Field of Classification Search
CPC combination set(s) only.
See application file for complete search history.

(56) References Cited

U.S. PATENT DOCUMENTS

| 2011/0130647 A1* | 6/2011 | Swartz | G01R 33/286 600/421 |
| 2012/0288820 A1* | 11/2012 | Choe | A61B 5/0555 433/29 |

OTHER PUBLICATIONS

Alfonsetti, et al., Versatile Coil Design and Positioning of Transverse-Field RF Surface Coils for Clinical 1.5-T MRI Applications, MAGMA, 2005, 18:69-75.
(Continued)

*Primary Examiner* — Katherine Fernandez
*Assistant Examiner* — Farshad Negarestan
(74) *Attorney, Agent, or Firm* — Quarles & Brady LLP (57) ABSTRACT

A system and method for producing an image using a radio frequency (RF) coil in a magnetic resonance imaging system (MRI). A static magnetic field ($B_0$) extends across a first and second region of interest (ROI). A local radio frequency (RF) coil, shaped like a dental arch, is positioned proximate to the ROIs, the ROIs being the upper and lower jaw of a subject. The RF coil and the subject are oriented in the static magnetic field ($B_0$) to align an axis extending through a loop of the coil with the $B_0$ direction of the static magnetic field extending across the ROIs. A pulse sequence is then performed with the MRI system and the RF coil to acquire imaging data from the ROIs simultaneously while using a transverse component of an excitation field ($B_1$). The image data is reconstructed to create an image of the ROIs.

11 Claims, 9 Drawing Sheets

(51) Int. Cl.
A61B 5/055 (2006.01)
G01R 33/341 (2006.01)
G01R 33/3415 (2006.01)

(56) References Cited

OTHER PUBLICATIONS

Alfonsetti, et al., Optimization of Multi-Element Transverse Field Radio Frequency Surface Coils, Measurement Science and Technology, 2006, 17(10):N53-N59.
Bergin, et al., Lung Parenchyma: Projection Reconstruction MR Imaging, Radiology, 1991, 179:777-781.
Boujraf, et al., Microstructural Assessment of Dental Tissues by Quantitative MRI Using Ultra-Short Echo Times (UTE): In-Vitro Evaluation, Proc. Intl. Soc. Mag. Reson. Med., 2009, 17:4520.
Bracher, et al., Feasibility of Ultra-Short Echo Time (UTE) Magnetic Resonance Imaging for Identification of Carious Lesions, Magnetic Resonance in Medicine, 2011, 66(2):538-545.
Bracher, et al., Ultrashort Echo Time (UTE) MRI for the Assessment of Caries Lesions, Dentomaxillofacial Radiology, 2013, 42, Mar. 21, 2012, pp. 1-11.
Collins, ImageJ for Microscopy, BioTechniques, 2007, 43:S25-S30.
Ferretti, et al., Dental Magnetic Resonance Imaging: Study of Impacted Mandibular Third Molars, Dentomaxillofacial Radiology, 2009, 38:387-392.
Garwood, et al., Capturing Signals from Fast-Relaxing Spins with Frequency-Swept MRI: SWIFT, Encyclopedia of Magnetic Resonance, Published by John Wiley & Sons, Ltd., 2012, pp. 1-13.
Gatehouse, et al., Magnetic Resonance Imaging of Short T2 Components in Tissue, Clinical Radiology, 2003, 58(1):1-19.
Grodzki, et al., Ultrashort Echo Time Imaging Using Pointwise Encoding Time Reduction With Radial Acquisition (PETRA), Magnetic Resonance in Medicine, 2012, 67:510-518.
Hafner, Fast Imaging in Liquids and Solids with the Back-Projection Low Angle ShoT (BLAST) Technique, Magnetic Resonance Imaging, 1994, 12(7):1047-1051.
Idiyatullin, et al., Fast and Quiet MRI Using a Swept Radiofrequency, Journal of Magnetic Resonance, 2006, 181(2):342-349.
Idiyatullin, et al., Direct MRI of Human Teeth by SWIFT, Proc. Intl. Soc. Mag. Reson. Med., 2007, 15:383.
Idiyatullin, et al., Gapped Pulses for Frequency-Swept MRI, Journal of Magnetic Resonance, 2008, 193(2):267-273.
Idiyatullin, et al., Dental MRI: Making the Invisible Visible, J. Endod., 2011, 37(6):745-752.
Kendi, et al., Transformation in Mandibular Imaging with Sweep Imaging with Fourier Transform Magnetic Resonance Imaging, Arch. Otolaryngol. Head Neck Surg. 2011, 137(9):916-919.
Kocsis, et al., Image Averaging of Flexible Fibrous Macromolecules: The Calthrin Triskelion has an Elastic Proximal Segment, Journal of Structural Biology, 1991, 107(1):6-14.
Kress, et al., Age- and Tooth-Related Pulp Cavity Signal Intensity Changes in Healthy Teeth: A Comparative Magnetic Resonance Imaging Analysis, Oral Surgery, Oral Medicine, Oral Pathology, Oral Radiology, and Endodontology, 2007, 103(1):134-137.
Kress, et al., Quantitative Analysis of MRI Signal Intensity as a Tool for Evaluating Tooth Pulp Vitality, Dentomaxillofacial Radiology, 2004, 33:241-244.
Lee, et al., Magnetic Resonance Imaging of Normal and Osteomyelitis in the Mandible: Assessment of Short Inversion Time Inversion Recovery Sequence, Oral Surgery, Oral Medicine, Oral Pathology, Oral Radiology and Endodontics, 2003, 96(4):499-507.
Lockhart, et al., Magnetic Resonance Imaging of Human Teeth, Journal of Endodontics, 1992, 18(5):237-244.
Madio, et al., Ultra-Fast Imaging Using Low Flip Angles and FIDs, Magnetic Resonance in Medicine, 1995, 34(4):525-529.
Nasel, et al., Localization of the Mandibular Neurovascular Bundle Using Dental Magnetic Resonance Imaging, Dentomaxillofacial Radiology, 1998, 27:305-307.
Nasel, et al., Technical Note. Dental MR Tomography of the Mandible, Journal of Computer Assisted Tomography, 1998, 22(3):498-502.
Olt, et al., Contrast-Enhanced Dental MRI for Visualization of the Teeth and Jaw, Magnetic Resonance in Medicine, 2004, 52(1):174-176.
Ploder, et al., Reperfusion of Autotransplanted Teeth—Comparison of Clinical Measurements by Means of Dental Magnetic Resonance Imaging, Oral Surgery, Oral Medicine, Oral Pathology, Oral Radiology, and Endodontology, 2001, 92(3):335-340.
Tannus, et al., Improved Performance of Frequency-Swept Pulses Using Offset-Independent Adiabaticity, Journal of Magnetic Resonance, Series A, 1996, 120(1):133-137.
Tutton, et al., MRI of the Teeth, The British Journal of Radiology, 2002, 75(894):552-562.
Tymofiyeva, et al., In Vivo MRI-Based Dental Impression Using an Intraoral RF Receiver Coil, Concepts in Magnetic Resonance Part B: Magnetic Resonance Engineering, 2008, 33B(4):244-251.
Tymofiyeva, et al., Three-Dimensional Localization of Impacted Teeth Using Magnetic Resonance Imaging, Clinical Oral Investigations, 2010, 14(2):169-176.
Vaughan, Chapter 6: Ultra High Field MRI: High-Frequency Coils, in Ultra High Field Magnetic Resonance Imaging, vol. 26, Springer US, 2006, pp. 127-161.
Weglarz, et al., 3D MR Imaging of Dental Cavities—An In Vitro Study, Solid State Nuclear Magnetic Resonance, 2004, 25(1-3):84-87.
Weiger, et al., MRI With Zero Echo Time: Hard Versus Sweep Pulse Excitation, Magnetic Resonance in Medicine, 2011, 66(2):379-389.
Weiger, et al., High-Resolution ZTE Imaging of Human Teeth, NMR in Biomedicine, 2012, 25(10):1144-1151.
Wu, et al., Water- and Fat-Suppressed Proton Projection MRI (WASPI) of Rat Femur Bone, Magnetic Resonance in Medicine, 2007, 57(3):554-567.

\* cited by examiner

SYSTEM AND METHOD FOR MULTI-ROI MRI IMAGING USING AN RF LOOP COIL

CROSS-REFERENCE TO RELATED APPLICATIONS

The present application is based on, claims priority to, and incorporates herein by reference in it entirety U.S. Provisional Application Ser. No. 61/756,886 filed Jan. 25, 2013, and entitled, "SYSTEM AND METHOD FOR MULTI-ROI MRI IMAGING USING AN RF LOOP COIL."

STATEMENT REGARDING FEDERALLY SPONSORED RESEARCH

This invention was made with government support under P41 RR008079 awarded by the National Institutes of Health. The government has certain rights in the invention.

BACKGROUND OF THE INVENTION

The field of the invention is magnetic resonance imaging (MRI) and systems. More particularly, the invention relates to a device and method for imaging multiple regions of interest (ROIs) using a radiofrequency (RF) coil.

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

MRI-based techniques are increasingly preferred over other imaging modalities in clinical medicine, for example, due to growing healthcare concerns over cumulative exposure to ionizing radiation, as is used in x-ray and computed tomography (CT) imaging. Even in dentistry applications, where x-ray has been a mainstay of clinical practice, MRI is growing in popularity.

Beyond the avoidance of ionizing radiation, MR techniques for diagnostic imaging in dentistry have become of greater interest due to new advances that have enabled direct imaging of densely calcified tissues of the human body, such as dentin and enamel. These tissues have low water content and, thus, a low fraction of protons to obtain signal from for MRI imaging. Also, these tissues have a quickly decaying signal and, thus, very short transverse relaxation times, $T_2$. In other words, the signal from mineralized dental tissue decays before MRI signal digitization occurs, resulting in MRI images with little or no image intensity. However, currently, there are at least four different and clinically viable MRI methods for obtaining images of densely calcified dental tissues, these include: i) Ultrashort TE (UTE), ii) Sweep Imaging with Fourier Transformation (SWIFT), iii) FID-projection imaging also called BLAST, RUFIS, WASPI, or zero TE (ZTE), and iv) combined PETRA techniques. Thus, dental MRI is a feasible technique for diagnostic imaging.

Dental MRI can be more informative than x-ray imaging techniques by visualizing, noninvasively and simultaneously, both hard and soft tissues in three dimensions. However, clinical MRI has yet to attain the resolution of CT imaging and, in particular cone beam CT (CBCT) imaging from 0.1-0.3 mm for all the regions of interest, such as for all teeth required for dental applications. The SNR and resolution for dental MRI is highly dependent on the configuration (i.e., filling factor) and performance of the radio frequency (RF) coil and field-of-view (FOV). For example, to image the mandible, extra-orally positioned surface coils, or head coils, are required, which have limited resolution and sensitivity and are expensive. As such, traditionally, MRI imaging has been restricted to imaging of the mandibular neurovascular bundle, vitality of the pulp structure, visualization of the anatomy and pathology of the dento-alveolar region, detection of osteomyelitis in the mandible, and the indirect imaging of highly mineralized tissue through contrast produced by an MRI-visible medium.

Also, in order to reach the necessary resolution, artifacts related to patient movement need to be minimized (including avoiding swallowing). Therefore the dental coil needs to be rigidly fixated in relation to the imaging system yet comfortable to prevent patient fatigue that results in fidgeting. The specifics of short $T_2$ imaging do not allow for the use of slice or slab selections, both to preserve signal from hard tissues having ultra-short $T_2$ and due to the three-dimensional radial free-induction decay acquisition strategy. Thus the acquired FOV must include the entire sensitive volume of the RF coil to avoid signal folding onto areas of interest in the image. The spatial resolution, which is the linear size of the image voxel, depends on the FOV and the reconstructed matrix size. To reach the necessary resolution, for example, 0.3 mm, the FOV should not exceed about 80 mm to 120 mm with $256^3$ to $384^3$ matrix sizes, respectively. However, increasing the matrix size is not practical because it is restricted by the clinical scan time, typically around 2-3 minutes for conventional 3D scanning. Thus, in dental applications using traditional head or neck coils, the necessary resolution will not be achieved. Therefore, a dedicated, localized surface coil design is needed.

The logical approach to imaging teeth would be to adopt existing surface coil designs with extra-oral placement adjacent to the area of interest. The diameter of such a receive coil should not exceed about 120 mm because it is limited by the size of the optimal FOV. The depth of the sensitive region in the axial direction, which is perpendicular to the plane of the surface coil, is limited to about the radius of the coil. To obtain an image of a right molar tooth, for example, such an extraoral coil could be positioned over the right cheek. For an average-sized patient, the distance between the coil and the molar teeth is between 30 and 50 mm, and as a result, sensitivity is significantly diminished. In addition, with the coil in this configuration, the cheek and buccal fat produce intense signals. Therefore, the resulting images contain more signals from less important structures of the mandible and maxilla and vice versa.

The resolution and signal-to-noise ratio (SNR) could be increased by using a loop coil positioned intra-orally, in the buccal vestibule that is between the teeth and adjacent cheek. By sacrificing some comfort, as well as some SNR, the intense signal from the cheek can be shielded out.

However, due to space restriction and the need for comfortable positioning of the coil, the root tips of the teeth are unavoidably outside the coil sensitive volume and not well visualized. Further, normal intraoral anatomy makes it difficult to position the coil posterior enough to obtain images of the most distal teeth in the mouth, and common variations of intraoral anatomy, such as the presence of buccal tori and frena, pose additional difficulties in positioning the coil. This suggests that using the buccal vestibule approach for RF coil placement is problematic for patient comfort and limits visualization of oral structures. Accommodating all patient sizes and anatomical variations would likely require multiple types and sizes of coils as well as repeated scans in order to obtain needed images Dental MRI continues to develop as an important imaging technique, however, it would be desirable to have a system and method for placement of a dental coil such that the sensitive volume of the coil covers the most important dental structures and excludes the less informative tissues (i.e., the cheeks, lips and tongue), as well as reduce patient discomfort and total time to image the areas of interest.

SUMMARY OF THE INVENTION

The present invention overcomes the aforementioned drawbacks by providing a system and method for placing a simple, yet efficient, intra-oral radio frequency (RF) coil between the teeth of the upper and lower jaws in the occlusal plane oriented orthogonally to the static magnetic field ($B_0$), while utilizing the transverse component of the $B_1$ field for transmitting and receiving the NMR signal to image the teeth and associated structures.

In accordance with one aspect of the invention, a magnetic resonance imaging (MRI) method is disclosed that involves acquiring an image of a subject from a first and second region of interest (ROI) simultaneously. The system has a static magnetic field having a $B_0$ direction and extending across the first and second ROI. The steps of the method include positioning a local radio frequency (RF) coil forming a loop proximate to the first and second ROI. The loop defines an axis extending through the loop and passing through a first side of the RF coil located proximate to the first ROI and through another side of the RF coil proximate to the second ROI and opposite the first side of the RF coil. The method further includes orienting the RF coil and the subject in the static magnetic field to align the axis extending through the loop with the $B_0$ direction of the static magnetic field extending across the first and second ROI. A pulse sequence is then performed with the MRI system and the RF coil to acquire imaging data from the first and second ROI simultaneously. The imaging data is then reconstructed to create an image of the subject including the first and second ROI.

In accordance with another aspect of the invention, a method for producing a dental image of a subject with an MRI system is disclosed. The steps of the method include providing an intra-oral RF coil in the shape of a human dental arch. The intra-oral RF coil is then positioned between the upper and lower jaw in an occlusal plate and orthogonal to a static magnetic field ($B_0$) of the MRI system. Further, a transverse component of an excitation field ($B_1$) generated using the MRI system is utilized to acquire image data from the upper and lower jaw. The transverse component of the $B_1$ field is parallel to the occlusal plane that the intra-oral RF coil is placed on. An image of the upper jaw and the lower jaw is then reconstructed from the image data.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
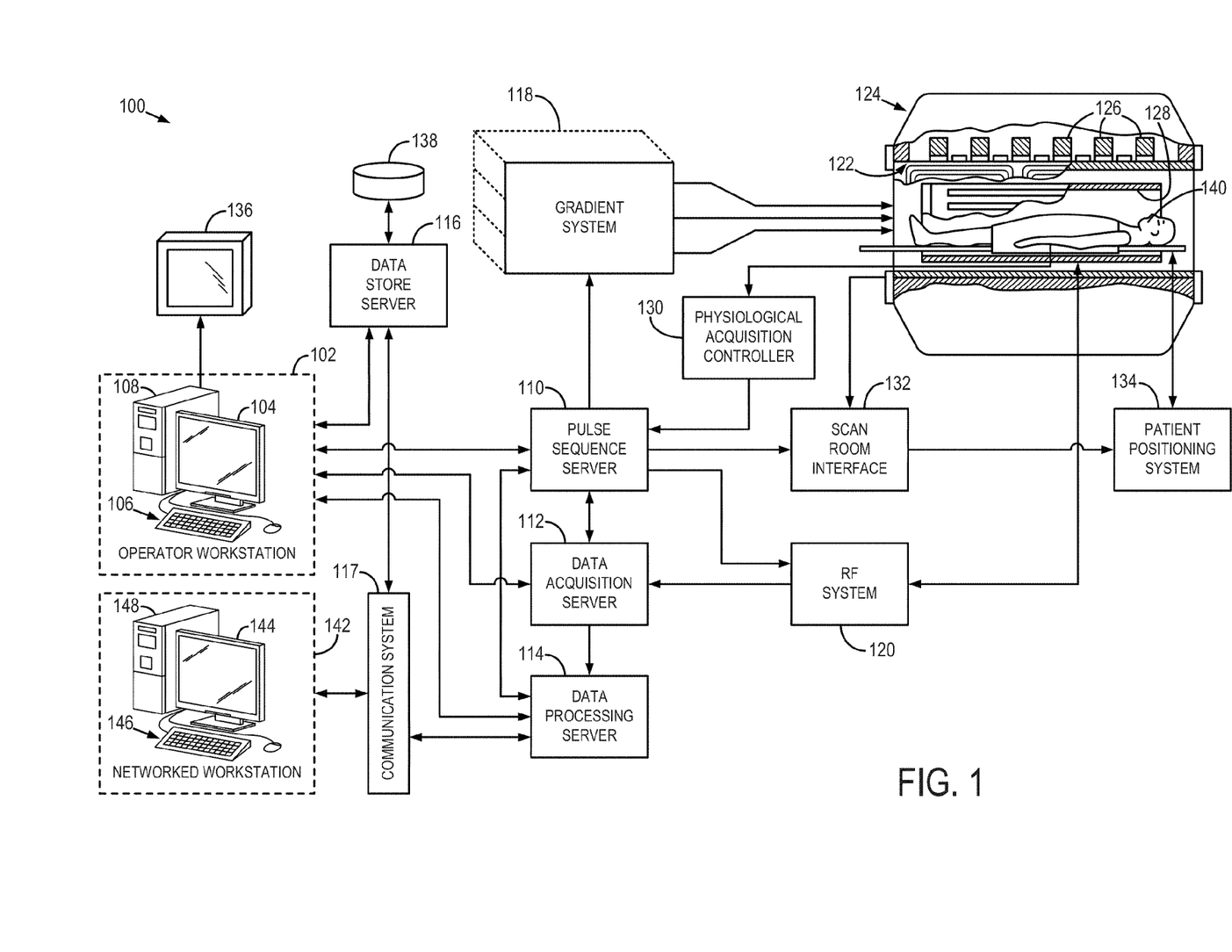
FIG. 1 is a block diagram of an MRI system which employs the present invention.

Referring particularly now to FIG. 1, an example of a magnetic resonance imaging (MRI) system 100 is illustrated. As will be described, the present invention can use an MRI system, such the illustrated MRI system 100, which is a general-purpose MRI system. Alternatively, the present invention may be used with specialized MRI systems, such as ones specifically designed for oral or dental imaging.

The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128. Though a whole-body coil 128 is illustrated because such whole-body coils 128 are commonly employed with general-purpose MRI systems, the present invention, as will be described, uses a local RF coil, such as an intra-oral RF coil 140.

RF waveforms are applied by the RF system 120 to the RF coil 128 or the intra-oral RF coil 140, in order to perform the prescribed magnetic resonance pulse sequence. Responsive magnetic resonance signals detected by the RF coils 128 and/or 140, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or the intra-oral RF coil 140.

The RF system 120 also includes one or more RF receiver channels. Each RF receiver channel includes an RF preamplifier that amplifies the magnetic resonance signal received by the coil 128/140 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \qquad (1)$$

and the phase of the received magnetic resonance signal may also be determined according to the following relationship:

$$\varphi = \tan^{-1}\left(\frac{Q}{I}\right). \qquad (2)$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Figure 2:
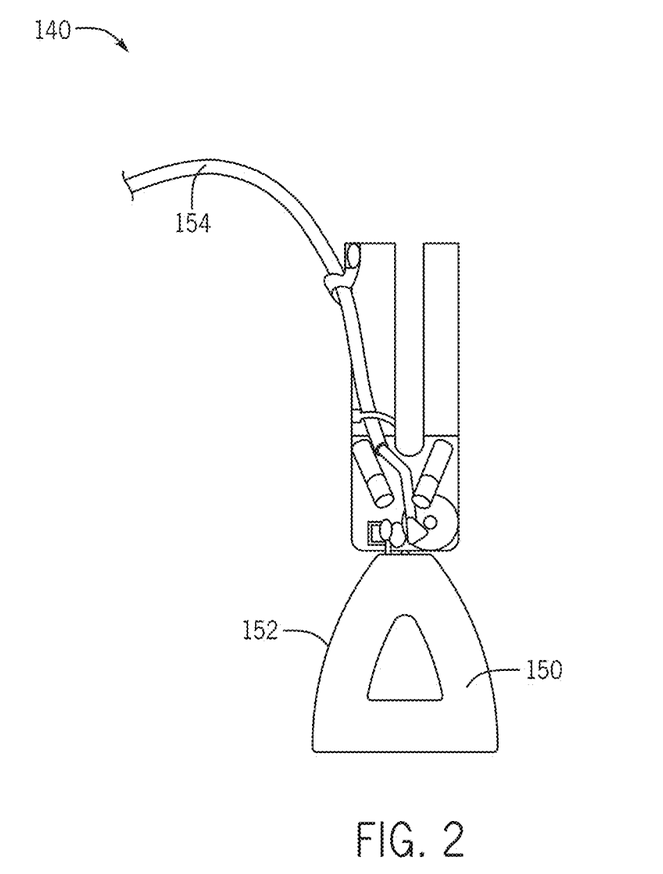
FIG. 2 is an illustration of an intra-oral radio frequency (RF) loop coil of the present invention designed to use a transverse component of the $B_1$ field.

An example of the intra-oral RF coil 140 in accordance with the present invention is illustrated in FIG. 2. The intra-oral RF coil 140 can include a single wire 154 forming a single loop 152 constructed with copper foil (not shown) of, for example, 10 mm width. The single loop 152 can be the shape and size of an average subject's maxillary arch with a radius of, for example, approximately 25 mm for an adult. The copper foil (not shown) can be covered by insulation 150, such as a foam adhesive, for patient comfort and protection from the single loop 152 when inserted between the upper and lower jaws of a patient in the occlusal plane.

In vivo SWIFT imaging data, as seen in FIGS. 6A-6D, can be acquired using the MRI system 100 shown in FIG. 1. The MRI system 100 can include a 4T (90 cm-bore) MRI scanner equipped with Varian DirectDrive™ console. The maximum ramp time and field gradient strengths of the gradient system 118 may be 0.4 milliseconds and 40 mT/m, respectively. The intra-oral RF coil 140 is positioned between the teeth of the upper and lower jaws of an average adult in the occlusal plane. However, for experimental purposes, a water phantom, comprised of a 150 mm diameter glass cylinder filled with tap water, was used. The intra-oral RF coil 140, electrically isolated by means of a plastic covering, was immersed in the tap water and fixed to the edges of the glass cylinder. The longitudinal and transverse components can then be imaged by changing the orientation of the glass cylinder, thereby avoiding changing the coil 140 tuning and loading conditions.

The Sweep imaging with Fourier Transformation (SWIFT) sequence can be used for imaging. Example acquisition parameters include: $b_w$=125 kHz, TR (time delay between the end of one acquisition and the start of the next acquisition)=2.65 ms, number of projections=131000, FOV=$12^3$ cm$^3$ and total acquisition time is 4.5 min. The nominal flip angle can be 8 degrees with acquisition 128 complex points during gapped HS2 pulse and continuous acquisition of 128 complex points after the pulse. Each spoke acquisition results in one center-out line of k-space after pre-processing (radial center-out k-space trajectory). The terminus of the radial spokes grouped in 128 interleaved spirals and acquired with Halton view order forms isotropically distributed points on a sphere. 3D radial SWIFT data can then be processed using a program developed in LabVIEW (National Instruments) and interpolated with a Kaiser-Bessel function onto a Cartesian grid utilizing MATLAB (Mathworks) mex code to a matrix of $384^3$ (yielding 0.3 mm nominal resolution). When using MATLAB, a Biot-Savart's magnetostatic approximation of the $B_1$ field can be used.

Figure 3:
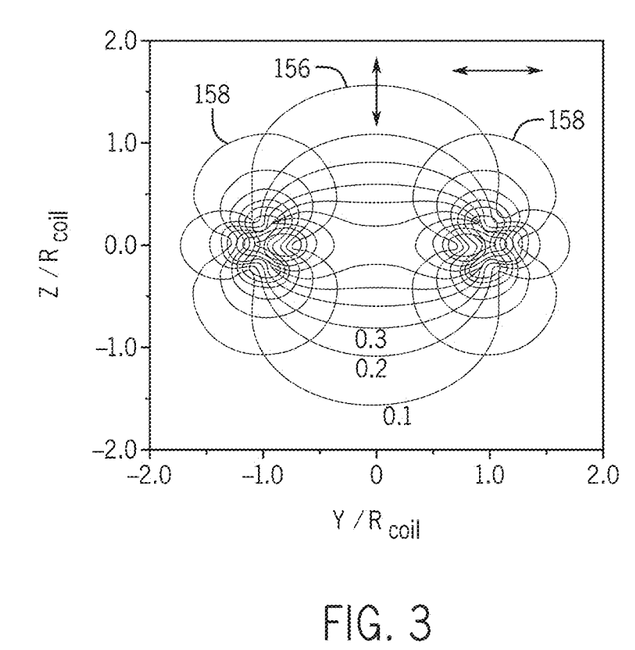
FIG. 3 is a graphic illustration of the longitudinal and traverse components of the $B_1$ field at the XZ plane created by the intra-oral RF loop coil located in the XY plane.

Referring now to FIG. 3, the calculated isocontour lines of the longitudinal component 156 of the $B_1$ field and the transverse component 158 of the $B_1$ field at the XZ plane created by the single loop surface coil 140 (not shown), of radius $R_{coil}$, located in the XY plane and centered at (0, 0, 0) is illustrated. In the XY plane and parallel planes, the isocontour lines are radially symmetrical and describe the circular shape. Viewed in the YZ plane the contours have differing symmetry for the two orthogonal components. The longitudinal component 156 describes a mirrored shape for each contour, with XY plane of symmetry. The transverse components 158 are presented as two circular shapes (also mirrored) at the position of each crossing of the coil 140 element of the YZ plane. They can be described as two toroidal volumes or "doughnuts" of sensitivity above and below the XY coil loop plane. The longitudinal component 156 may have higher values at the center of the coil 140 (and Z axis) relative to the transverse component 158, and overall may have about 10 percent deeper penetration (measured from the Y plane) relative to transverse component 158. For excitation and detection in MRI either the longitudinal component 156 or transverse components 158 (or combination) of the surface coil $B_1$ can be used, and this depends on the orientation of the coil 140 plane relative to the Zeeman field, $B_0$.

Traditionally, the plane of the coil 140 is oriented parallel to the $B_0$ field 166 (not shown) to exploit the longitudinal component 156 of the $B_1$ field. However, in accordance with one aspect of the present invention, the coil 140 is oriented in the occlusal plane, orthogonal to the $B_0$ field 166, and utilizing the transverse component of the $B_1$ field to obtain diagnostic images from both sides (i.e., both the upper and lower teeth) of the coil 140.

Figure 4A:
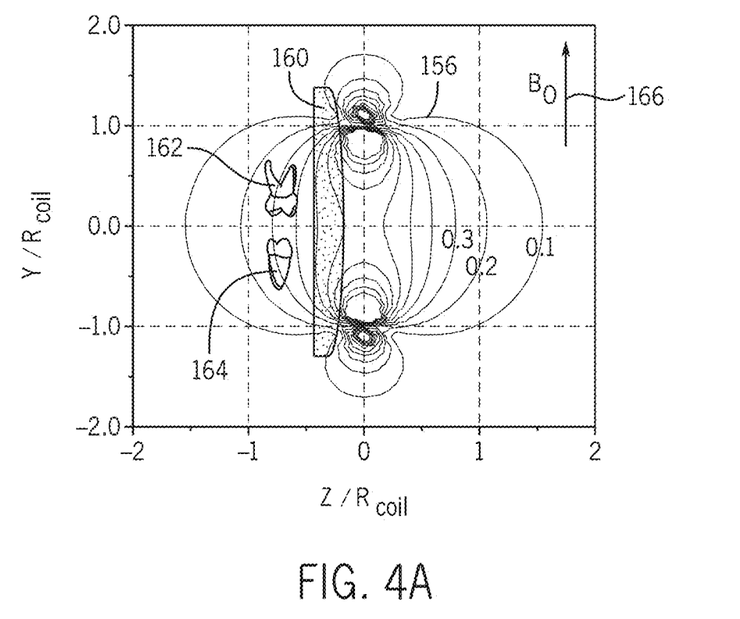
FIG. 4A is a schematic illustration of the longitudinal component of the $B_1$ field and objects of the upper and lower jaws of interest to be imaged with an extra-oral coil positioned over the cheek in the molar region.
Figure 4B:
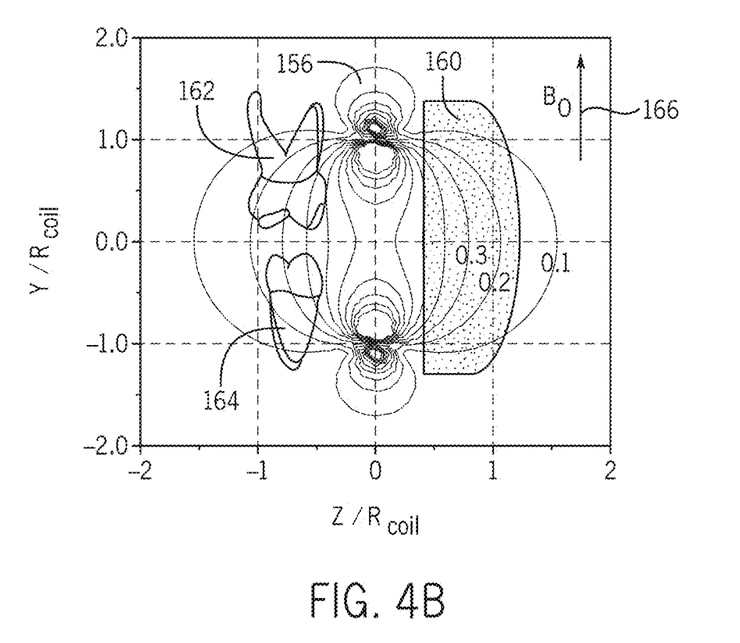
FIG. 4B is a schematic illustration of the longitudinal component of the $B_1$ field and objects of the upper and lower jaws of interest to be imaged with an intra-oral coil positioned within the buccal vestibule adjacent to the molars.

In dental MRI there are two known ways of using a surface coil 140 to obtain diagnostic images; namely, extra-oral positioning and intra-oral positioning, as schematically presented in FIGS. 4A and 4B, respectively. FIGS. 4A and 4B display the longitudinal component 156 of the $B_1$ field. In FIG. 4A, the coil 140 (not shown) is disposed extra-orally over the check in the molar region 160 of a patient, parallel to the $B_0$ field 166 (indicated by the arrow orientated upward), in order to obtain diagnostic images of the teeth and structures of interest in the upper jaw 162 and the lower jaw 164. The main advantage of extra-oral positioning of the coil 140 is the patient's comfort, however low filling factor, low resolution, a low SNR and high amplitude signal from non-informative soft tissue are also seen. Alternatively, in FIG. 4B, the coil 140 (not shown) is disposed intra-orally within the buccal vestibule adjacent to the molar teeth 160 of the patient, parallel to the $B_0$ field 166 (indicated by the arrow orientated upward), in order to obtain diagnostic images of the teeth and structures of interest in the upper jaw 162 and the lower jaw 164. When the coil 140 is positioned intra-orally, the SNR is high and the signal produced in the molar region 160 is still high, but could be shielded out. However, as shown in FIG. 4B, there is a low SNR at the tips of the teeth in the upper 162 and lower 164 jaws which may be valuable to image.

Figure 5:
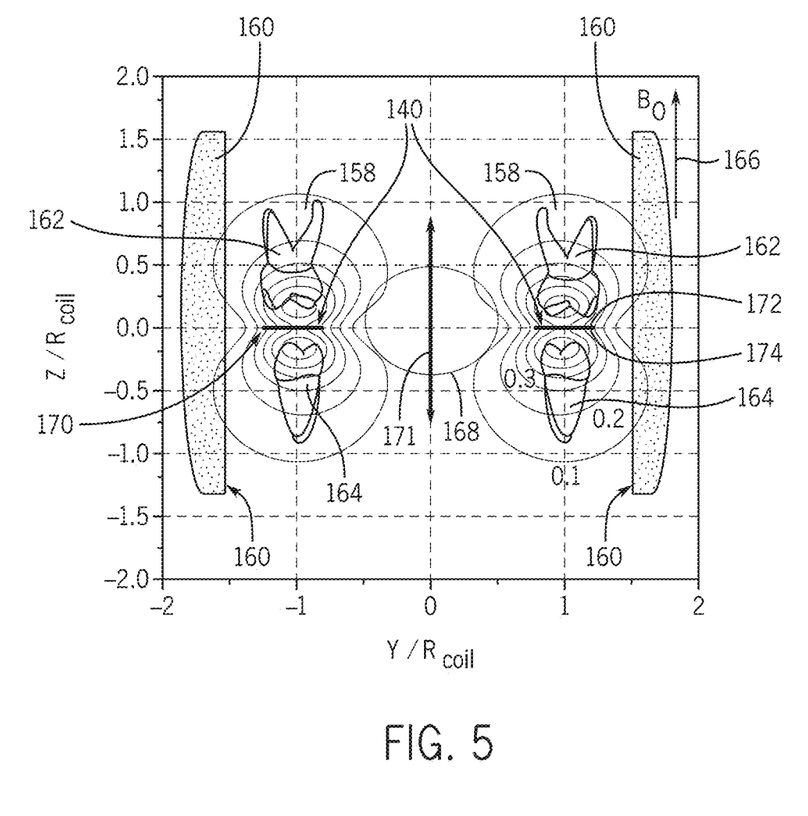
FIG. 5 is a schematic illustration of the transverse component of the $B_1$ field and the intra-oral RF loop coil positioned in the occlusal plane, orthogonal to the $B_0$ field.

Referring now to FIG. 5, showing one embodiment of the present invention, the intra-oral coil 140 may be positioned in an occlusal plane 170 between the upper jaw 162 and the lower jaw 164, such that an axis 171 of the coil extending through the loop of the coil is parallel to the $B_0$ field 166. The intra-oral coil 140 is positioned orthogonal to the $B_0$ field 166 and is utilizing the transverse component 158 of the $B_1$ field. As shown in FIG. 5, there are transverse components 158 of the $B_1$ field about the intra-oral coil 140 that excite spins in the teeth and structures of the upper jaw 162 and the lower jaw 164 while limiting visibility of the tongue 168, and other soft tissue with high lipid and water content in the molar region 160. The tips of the teeth of the upper 162 and lower 164 jaws have a higher SNR when the intra-oral coil 140 is positioned in the occlusal plane 170, compared to a lower SNR when the intra-oral coil 140 is positioned longitudinally on the molar region 160 as shown in FIG. 4B. Also, shown in FIG. 5, signals from the transverse components 158 of the $B_1$ field are generated on both an upper (or first) side 172 and a lower (or second) side 174 of the intra-oral coil 140. This facilitates imaging of the relevant teeth and structures of both the upper 162 and lower 164 jaw which is desirable.

Further, placement of the coil between the teeth in the occlusal plane such that the coil is orthogonal to the static magnetic field, $B_0$, is contrary to traditional orientation of surface coils where it is desirable to only receive signals from one side of the coil and mitigate any signal from the other side of the coil. That is, conventionally, all surface coils used a $B_1$ field component oriented longitudinally to the coil's axis (i.e., oriented with the coil's plane parallel to the Zeeman, $B_0$ field) and it is the $B_1$ field component in the direction of the coil axis that produces the majority of the field utilized for MRI. For most dental applications this orientation is optimal because the sensitive volume of the coil is close to spherical and allows images within the area to be captured. Historically, even though the sensitive volume of a loop coil is approximately spherical, it is called a surface coil, due to the fact that images are usually obtained from only one side of the loop.

The above-described coil system 140 can be used with a general-purpose or specialized MR system. In either context, the coil 140 may be used in a transmit/receive or receive-only configuration. When used for receive only, a body coil, head coil, or other coil may be used as the transmit coil and the above-described coil 140 is used as the receive-only coil. When the above-described coil 140 is used as a transmit/receive coil oriented perpendicular to the $B_0$ field, the longitudinal component of the $B_1$ field becomes unusable because it is parallel to the $B_0$ field and does not excite spins. But at the same time, the transverse component of the $B_1$ field should be considered. That is, there are transverse components of the $B_1$ field about the present intra-oral RF coil itself that excite spins in the teeth based on appropriate coil geometry and does not excite spins in the tongue, cheeks, and other soft tissue with high water and lipid content.

As described above, the intra-oral RF coil of the present invention may be configured as a single loop surface coil, where the plane of the coil can be oriented orthogonally to Zeeman field, $B_0$. The shape of the NMR sensitivity volume of such a coil resembles two adjacent fields, which is not a traditional configuration, that represents the two arches of the human jaws. The sensitive volume of the coil in the occlusal position is high for the relevant dental structures and is significantly diminished at the check, lips, and tongue which are less informative structures with intense water and lipid signals. The orientation of the coil in the occlusal plane is advantageous since spins can be excited in the teeth of both the upper and the lower jaw, such that both can be imaged simultaneously.

Figure 6A:
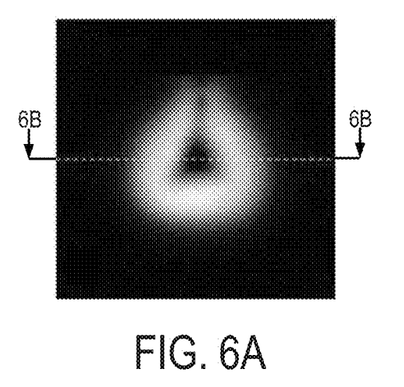
FIG. 6A is an image of a plane of a surface coil using the transverse component of the $B_1$ field.
Figure 6B:
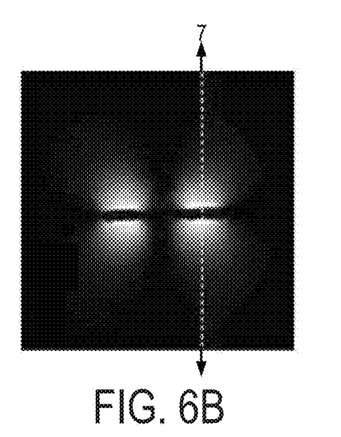
FIG. 6B is a cross-sectional image of the position of a slice along line 6B of FIG. 6A.
Figure 6C:
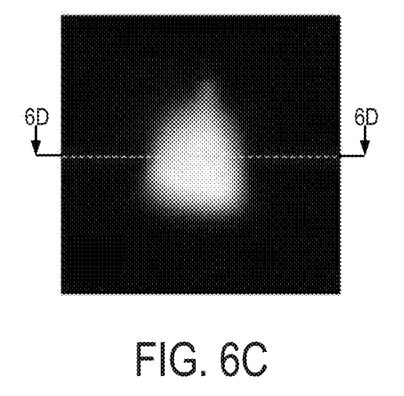
FIG. 6C is an image of the plane of a surface coil using the longitudinal component of the $B_1$ field.
Figure 6D:
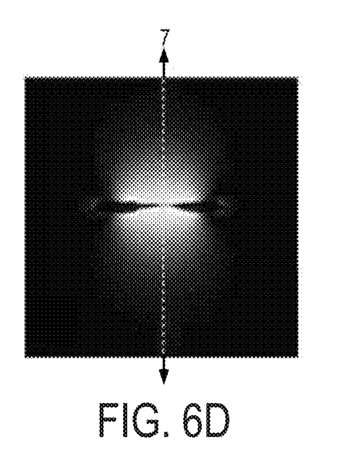
FIG. 6D is a cross-sectional image of the position of the slice along line 6D of FIG. 6C.
Figure 7:
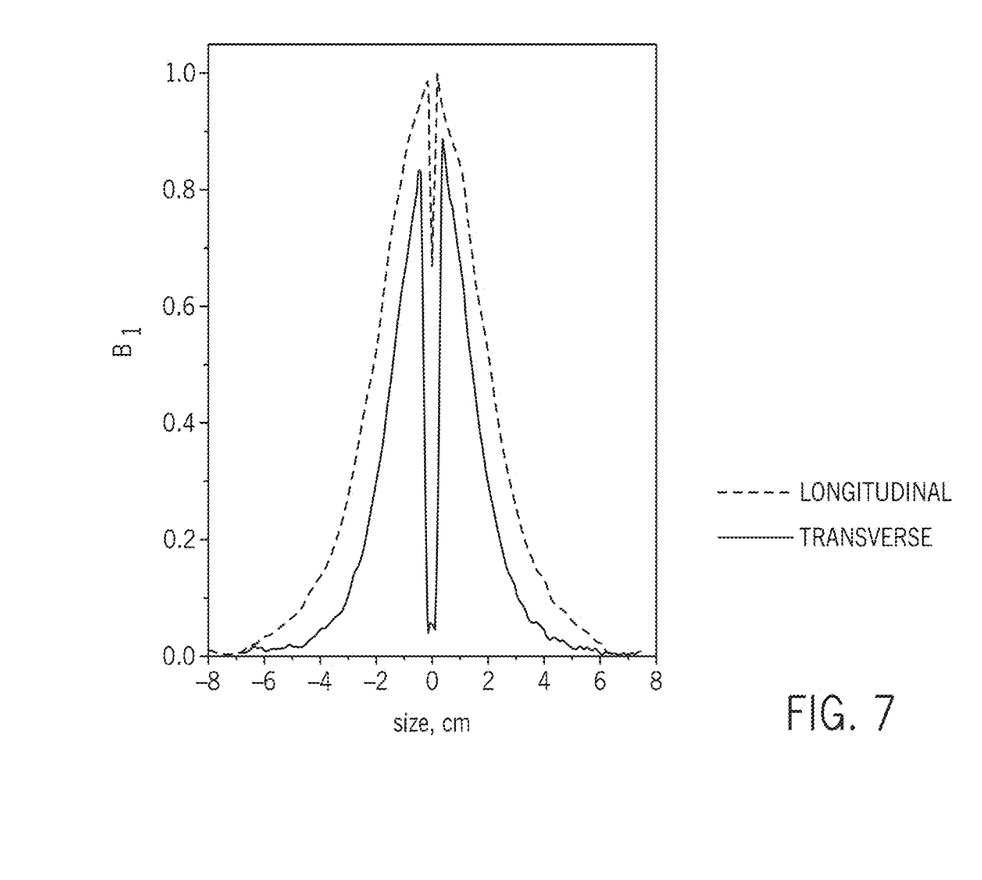
FIG. 7 is a graphic display of the intensity profiles taken along line 7 of FIGS. 6B and 6D.

To further show the benefits of the present invention, FIGS. 6A-D and 7 show a comparison of sensitive volumes of an intra-oral coil 140 in two orthogonal positions. FIG. 7 displays a sensitivity map of the intra-oral coil 140 using the transverse components 158 of the $B_1$ field (see FIGS. 6A and 6B) and the longitudinal components 156 of the $B_1$ field (see FIGS. 6B and 6C) in the coil plane of FIGS. 6A and 6C and orthogonally to the coil plane (see FIGS. 6B and 6D). Lines 6B and 6D shown in FIGS. 6A and 6C represent the position of slices in FIGS. 6B and 6D, respectively. The shape of the NMR sensitive volume shown in FIGS. 6B and 6D resembles two adjacent doughnuts and/or two arches of a human jaw. Line 7 shown in FIGS. 6B and 6D represent the position of the intensity profiles plotted in FIG. 7.

The graph in FIG. 7 shows the signal strength of the $B_1$ field on the vertical axis and the distance from the tongue 168 (shown at 0 cm) to the molar regions 160 on the horizontal axis. The graph shows that the molar region 160 and the tongue 168 appear to have a low intensity, and the objects of the upper 162 and lower 164 jaw have a higher intensity for both the longitudinal component 156 and the transverse component 158 of the $B_1$ field. Thus, the sensitivity of the intra-oral coil 140 in the occlusal plane is high for the relevant dental structures and is significantly diminished at the molar region 160, lips, and tongue 168.

Figure 8A:
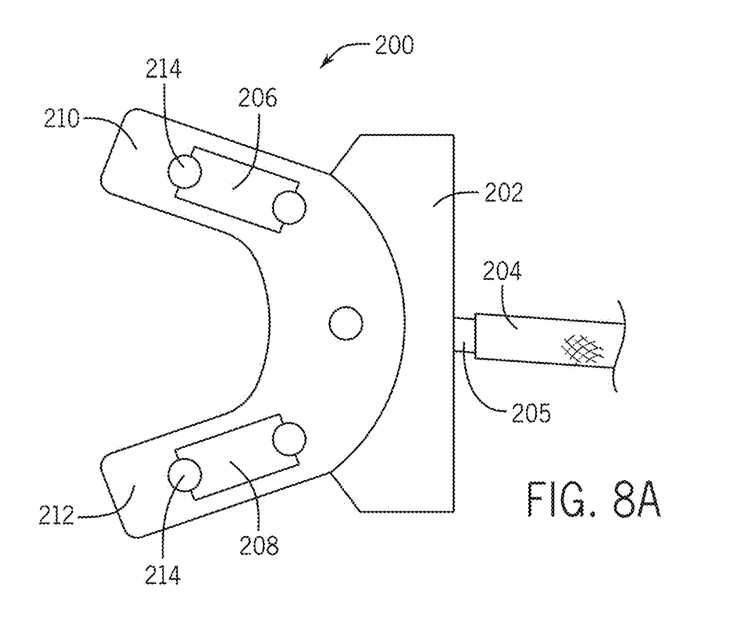
FIG. 8A is an illustration of a top view of an intra-oral coil having a resonant dipolar antenna embedded into a dental bite plate and non-magnetic air core inductors according to another embodiment of the present invention.
Figure 8B:
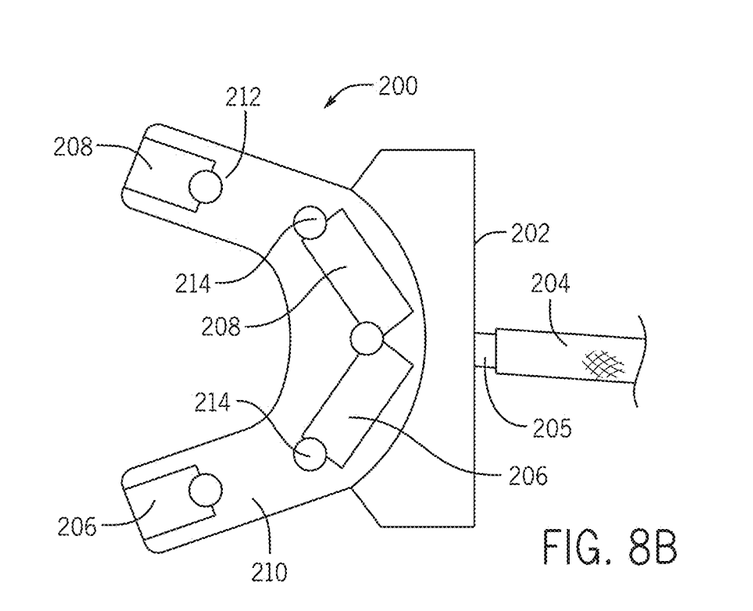
FIG. 8B is an illustration of a bottom view of the intra-oral coil of FIG. 8A.

Referring now to FIGS. 8A and 8B, an example of an intra-oral dipolar coil 200 in accordance with another embodiment of the present invention is shown. The intra-oral dipolar coil 200 may be a resonant dipolar antenna, for example, that is electrically isolated and embedded into a dental bite plate 202 and having a cable 204, such as a coaxial cable, attached thereto. The cable 204 may include a central wire (not shown) that connects with a first wire 206 and a ground wire 205 of the cable 204 along with a second wire 208, both constructed with copper foil, for example. Alternatively, the first wire 206 and the second wire 208 may be non-magnetic air core inductors, for example. The first wire 206 extends along a first portion 210 of the dental bite plate 202, and the second wire extends along a second portion 212 of the dental bite plate 202. Thus, the first wire 206 and the second wire 208 form the shape and size of an average subject's maxillary arch. The first wire 206 and the second wire 208 may be covered by insulation (not shown) for patient comfort and protection from the first wire 206 and the second wire 208 when inserted between the upper and lower jaws of a patient in the occlusal plane.

In addition, the intra-oral dipolar coil 200 may include apertures 214 that extend through the dental bite plate 202. The apertures 214 may provide openings through which the first wire 206 and the second wire 208 may extend through. The apertures 214 may be distributed along the first portion 210 and the second portion 212 of the dental bite plate 202 so that the first wire 206 and the second wire 208 align with the subject's teeth. Advantageously, since the intra-oral dipolar coil 200 does not require the conductive physical connection of the single loop 152, shown in FIG. 2, across the subject's tongue, the intra-oral dipolar coil 200, as shown in FIGS. 8A and 8B, may provide the subject with free movement of the tongue. Thus, the intra-oral dipolar coil 200 may allow the subject to swallow with a secure bite on the intra-oral dipolar coil 200 and may also be better tolerated by the subject.

The intra-oral dipolar coil 200 shown in FIGS. 8A and 8B may utilize the primary first lambda-half resonance, however, higher resonance modes may be used. The MRI system used with the intra-oral dipolar coil 200 may include a 1.5T, 3T, or 4T MRI scanner, for example, operating at frequencies of 64 MHz, 127 MHz, 170 MHz, respectively. While using these operating frequencies, the antenna inductance may be physically distributed.

A dental bite plate 202 and having a cable 204, such as a coaxial cable, may be attached thereto. The cable 204 may include a central wire (not shown) that connects with a first wire 206 and a ground wire 205 of the cable 204 along with a second wire 208, both constructed with copper foil, for example.

Figure 9:
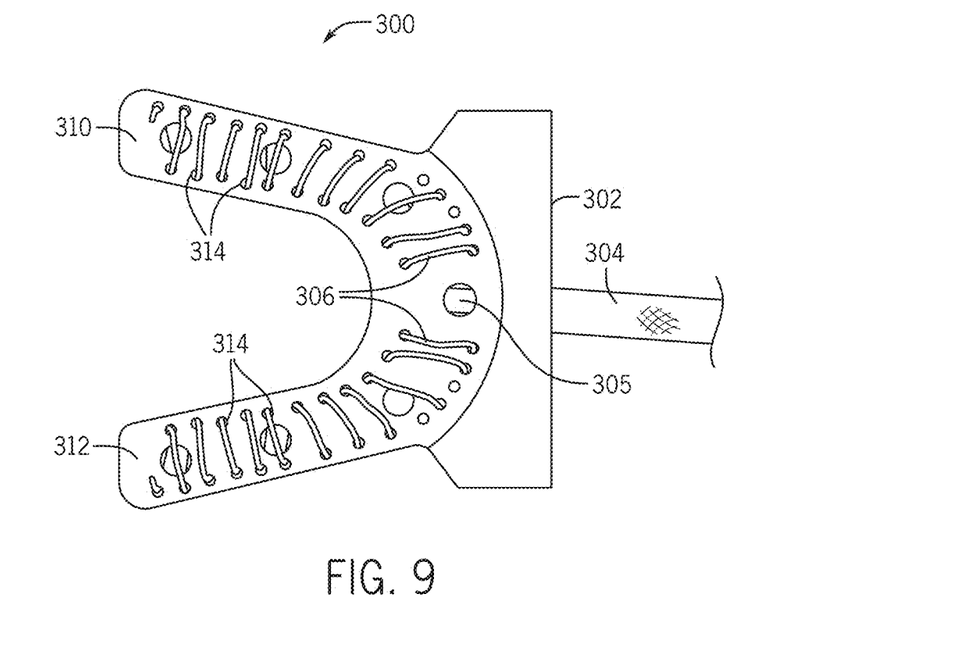
FIG. 9 is an illustration of an intra-oral coil having a resonant dipolar antenna embedded into a dental bite plate and inductors coiled about the bite plate according to another embodiment of the present invention.

Referring now to FIG. 9, another example of an intra-oral dipolar coil 300 is shown. The intra-oral dipolar coil 300 may be a resonant dipolar antenna, for example, that is electrically isolated and embedded into a dental bite plate 302 and having a cable 304, such as a coaxial cable, attached thereto. The cable 304 is coupled to a wire 306 constructed with copper, for example. A central wire (not shown) of the cable 304 extends along a first portion 310 of the dental bite plate 302 and a ground wire 305 of the cable 304 extends along a second portion 312 of the dental bite plate 302. Thus, the wire 306 forms the shape and size of an average subject's maxillary arch. The wire 306 may be covered by insulation (not shown) for patient comfort and protection when the intra-oral dipolar coil 300 is inserted between the upper and lower jaws of a patient in the occlusal plane. The intra-oral dipolar coil 300 may include apertures 314 that extend through the dental bite plate 302. The apertures 314 may provide openings through which the wire 306 is coiled through. Again, since the intra-oral dipolar coil 300 does not require the conductive physical connection of the single loop 152, shown in FIG. 2, across the subject's tongue, the intra-oral dipolar coil 300, as shown in FIG. 9, may provide the subject with free movement of the tongue. Thus, the intra-oral dipolar coil 300 may allow the subject to swallow with a secure bite on the intra-oral dipolar coil 300 and may also be better tolerated by the subject.

Figure 10:
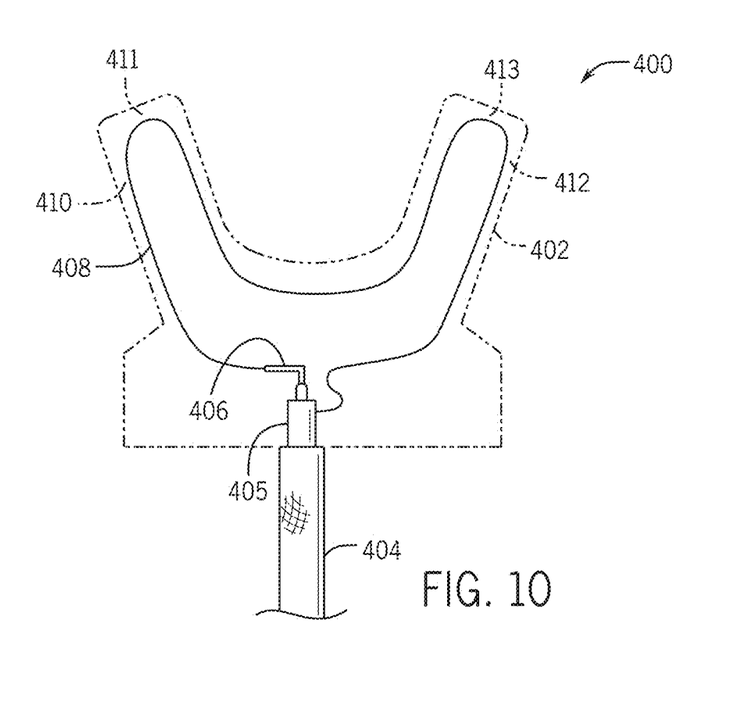
FIG. 10 is an illustration of an intra-oral coil having a resonant folded dipolar antenna according to another embodiment of the present invention.

Referring now to FIG. 10, another example of an intra-oral folded dipolar coil 400 is shown. The intra-oral folded dipolar coil 400 may be a resonant folded dipolar antenna, for example, that is electrically isolated and embedded into a dental bite plate 402 and having a cable 404, such as a coaxial cable, attached thereto. The cable 404 may be coupled to a wire 406 constructed with copper, for example. A central wire 408 of the cable 404 extends along a first portion 410 of the dental bite plate 402 and folds at a first end portion 411. The central wire 408 continues along the first portion 410 and continues to extend along a second portion 412 of the dental bite plate 402 where it folds again at a second end portion 413 of the dental bite plate 402. The central wire 408 continues to extend along the second portion 412 of the dental bite plate 402 and attaches to a ground wire 405 of the cable 404. Thus, the wire 408 forms the shape and size of an average subject's maxillary arch. The wire 408 may be covered by insulation (not shown) for patient comfort and protection when the intra-oral folded dipolar coil 400 is inserted between the upper and lower jaws of a patient in the occlusal plane. The intra-oral folded dipolar coil 400 may include apertures (not shown) that extend through the dental bite plate 402. The apertures may provide openings through which the wire 408 is coiled through. Again, since the intra-oral folded dipolar coil 400 does not require the conductive physical connection of the single loop, shown in FIG. 2, across the subject's tongue, the intra-oral folded dipolar coil 400, as shown in FIG. 10, may provide the subject with free movement of the tongue. Thus, the intra-oral folded dipolar coil 400 may allow the subject to swallow with a secure bite on the intra-oral dipolar coil 400 and may also be better tolerated by the subject.

Returning now to FIG. 5, the foregoing demonstrated that the transverse component 158 of the $B_1$ field of a surface coil 140 can effectively be used for the imaging of teeth and associated structures of the upper 162 and lower 164 jaws. Further, the sensitivity volume of an intra-oral coil 140 in the occlusion plane 170, positioned in between the teeth of the upper 162 and lower 164 jaws, encompasses the most important dental structures (i.e., teeth and jaws) and almost excludes the molar region 160, lips and tongue 168, which usually have less informative, but very intense signals due to their higher proton density. The present invention further demonstrates an intra-oral coil 140, that when inserted in between the teeth of the upper 162 and lower 164 jaws, patient discomfort is inhibited.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing a dental image of a subject with a magnetic resonance imaging (MRI) system, the steps comprising:
   a) providing an intra-oral radio frequency (RF) coil, the intra-oral RF coil being a shape of a human dental arch;
   b) positioning the intra-oral RF coil between an upper jaw and a lower jaw of the subject in an occlusal plane, wherein the intra-oral RF coil extends along the occlusal plane and is orthogonal to a static magnetic field (B0) of the MRI system;
   c) acquiring image data from the upper jaw and the lower jaw utilizing a transverse component of an excitation field (B1) generated using the MRI system, the transverse component of the B1 field being parallel to the occlusal plane that the intra-oral RF coil is positioned in; and
   d) reconstructing an image of the upper jaw and the lower jaw from the image data.

2. The method of claim 1 wherein providing the intra-oral RF coil includes providing a single loop using a single wire constructed of copper, the single loop being the shape of the dental arch.

3. The method of claim 2 further comprising the step of applying insulation to the single loop of the intra-oral RF coil to protect the single loop from the upper jaw and the lower jaw.

4. The method of claim 1 wherein the intra-oral RF coil includes a radius of about 25 millimeters.

5. The method of claim 1 wherein utilizing the transverse component of the B1 field includes exciting spins in at least one of teeth and structures of the upper and lower jaw while limiting visibility of soft tissues having high lipid and water content in the upper and lower jaw.

6. The method of claim 5 wherein limiting visibility of soft tissues includes limiting visibility of at least one of the subject's lips, tongue, malar region and cheek.

7. The method of claim 1 wherein positioning the intra-oral RF coil between the upper jaw and the lower jaw provides a sensitive volume about the intra-oral RF coil, the sensitive volume including relevant structures of the upper jaw and the lower jaw.

8. The method of claim 1 wherein reconstructing the image includes creating three dimensional image data of the upper jaw and the lower jaw.

9. The method of claim 1 wherein acquiring the image data comprises performing a pulse sequence, using the MRI system, that utilizes at least one of a Sweep imaging with Fourier Transformation (SWIFT) sequence and a short T2 sensitive sequence to create three dimensional radial data.

10. The method of claim 1 wherein providing the intra-oral RF coil includes providing a dipolar coil using at least two wires constructed of copper, the dipolar coil being the shape of the human dental arch.

11. The method of claim 1 wherein providing the intra-oral RF coil includes providing a folded dipolar coil using a single wire loop constructed of copper, the single wire loop being the shape of the human dental arch.

\* \* \* \* \*